(12) United States Patent
Rowe

(10) Patent No.: US 11,731,269 B1
(45) Date of Patent: Aug. 22, 2023

(54) ARTIFICIAL MUSCLES COMPRISING AN ELECTRODE PAIR AND A CLAMPING DEVICE FOR COMPRESSING THE ELECTRODE PAIR

(71) Applicant: Toyota Motor Engineering & Manufacturing North America, Inc., Plano, TX (US)

(72) Inventor: Michael P. Rowe, Pinckney, MI (US)

(73) Assignee: Toyota Motor Engineering & Manufacturing North America, Inc., Plano, TX (US)

( * ) Notice: Subject to any disclaimer, the term of this patent is extended or adjusted under 35 U.S.C. 154(b) by 0 days.

(21) Appl. No.: 17/590,376

(22) Filed: Feb. 1, 2022

(51) Int. Cl.
| | |
|---|---|
| *B25J 9/14* | (2006.01) |
| *F03G 7/06* | (2006.01) |
| *B25J 9/10* | (2006.01) |
| *A61B 34/00* | (2016.01) |

(52) U.S. Cl.
CPC ............... *B25J 9/142* (2013.01); *A61B 34/70* (2016.02); *B25J 9/1075* (2013.01); *F03G 7/0645* (2021.08)

(58) Field of Classification Search
CPC ......... B25J 9/142; B25J 9/1075; A61B 34/70; F03G 7/0645; F15B 15/103
See application file for complete search history.

(56) References Cited

U.S. PATENT DOCUMENTS

| | | | |
|---|---|---|---|
| 10,995,779 B2 * | 5/2021 | Keplinger | H02N 1/006 |
| 2021/0172460 A1 * | 6/2021 | Keplinger | F15B 5/006 |
| 2021/0237809 A1 | 8/2021 | Rowe et al. | |
| 2021/0370499 A1 | 12/2021 | Rowe et al. | |

FOREIGN PATENT DOCUMENTS

| | | | | |
|---|---|---|---|---|
| JP | 4385091 B2 | 12/2009 | | |
| SK | 6547 Y1 | 10/2013 | | |
| WO | 2001006579 A2 | 1/2001 | | |
| WO | 2007007616 A1 | 1/2007 | | |
| WO | WO-2007007616 A1 * | 1/2007 | ........... | B81B 3/0021 |
| WO | 2019173227 A1 | 9/2019 | | |

* cited by examiner

*Primary Examiner* — Randell J Krug
(74) *Attorney, Agent, or Firm* — Dinsmore & Shohl LLP

(57) ABSTRACT

An artificial muscle includes a housing including an electrode region and an expandable fluid region; an electrode pair positioned in the electrode region of the housing, the electrode pair comprising a first electrode positioned adjacent a first surface of the housing and a second electrode positioned adjacent a second surface of the housing, the first electrode and the second electrode each having a first end proximate the expandable fluid region and a second end opposite the expandable fluid region; a dielectric fluid housed within the housing; and a clamping device applying a force against the first electrode and the second electrode at the second end of the first electrode and the second electrode, wherein the electrode pair is actuatable between a non-actuated state and an actuated state such that actuation from the non-actuated state to the actuated state directs the dielectric fluid into the expandable fluid region.

20 Claims, 10 Drawing Sheets

ARTIFICIAL MUSCLES COMPRISING AN ELECTRODE PAIR AND A CLAMPING DEVICE FOR COMPRESSING THE ELECTRODE PAIR

TECHNICAL FIELD

The present specification generally relates to apparatus and methods for focused inflation on at least one surface of a device, and, more specifically, apparatus and methods for utilizing an electrode pair to direct a fluid to inflate the device.

BACKGROUND

Current robotic technologies rely on rigid components, such as servomotors to perform tasks, often in a structured environment. This rigidity presents limitations in many robotic applications, caused, at least in part, by the weight-to-power ratio of servomotors and other rigid robotics devices. The field of soft robotics improves on these limitations by using artificial muscles and other soft actuators. Artificial muscles attempt to mimic the versatility, performance, and reliability of a biological muscle. Some artificial muscles rely on fluidic actuators, but fluidic actuators require a supply of pressurized gas or liquid, and fluid transport must occur through systems of channels and tubes, limiting the speed and efficiency of the artificial muscles. Other artificial muscles use thermally activated polymer fibers, but these are difficult to control and operate at low efficiencies. Additionally, any space or gap formed between an electrode pair of the artificial muscles may result in an increased voltage required to close the gap and thus actuate the artificial muscles.

Accordingly, a need exists for improved artificial muscles with increased actuator power per unit volume by reducing the existence of any gaps between an electrode pair of the artificial muscles.

SUMMARY

In one embodiment, an artificial muscle includes: a housing including an electrode region and an expandable fluid region; an electrode pair positioned in the electrode region of the housing, the electrode pair including a first electrode positioned adjacent a first surface of the housing and a second electrode positioned adjacent a second surface of the housing, the first electrode and the second electrode each having a first end proximate the expandable fluid region and a second end opposite the expandable fluid region; a dielectric fluid housed within the housing; and a clamping device applying a force against the first electrode and the second electrode at the second end of the first electrode and the second electrode, wherein the electrode pair is actuatable between a non-actuated state and an actuated state such that actuation from the non-actuated state to the actuated state directs the dielectric fluid into the expandable fluid region.

In another embodiment, an artificial muscle includes: a housing including an electrode region and an expandable fluid region; an electrode pair positioned in the electrode region of the housing, the electrode pair including a first electrode fixed to a first surface of the housing and a second electrode fixed to a second surface of the housing, at least one of the first electrode and the second electrode including a central opening encircling the expandable fluid region, the first electrode and the second electrode each having a first end proximate the expandable fluid region and a second end opposite the expandable fluid region; a dielectric fluid housed within the housing; and a clamping device applying a force against the first electrode and the second electrode at the second end of the first electrode and the second electrode to reduce a gap between the second end of the first electrode and the second end of the second electrode, wherein the electrode pair is actuatable between a non-actuated state and an actuated state such that actuation from the non-actuated state to the actuated state directs the dielectric fluid into the expandable fluid region.

In yet another embodiment, a method for actuating an artificial muscle assembly includes generating a voltage using a power supply electrically coupled to an electrode pair of an artificial muscle, the artificial muscle including: a housing with an electrode region and an expandable fluid region, the electrode pair is positioned in the electrode region of the housing, the electrode pair including a first electrode positioned adjacent a first surface of the housing and a second electrode positioned adjacent a second surface of the housing, the first electrode and the second electrode each having a first end proximate the expandable fluid region and a second end opposite the expandable fluid region; a clamping device applying a force against the first electrode and the second electrode at the second end of the first electrode and the second electrode; and a dielectric fluid housed within the housing, and applying the voltage to the electrode pair of the artificial muscle, thereby actuating the electrode pair from a non-actuated state and an actuated state such that the dielectric fluid is directed into the expandable fluid region of the housing and expands the expandable fluid region.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1:
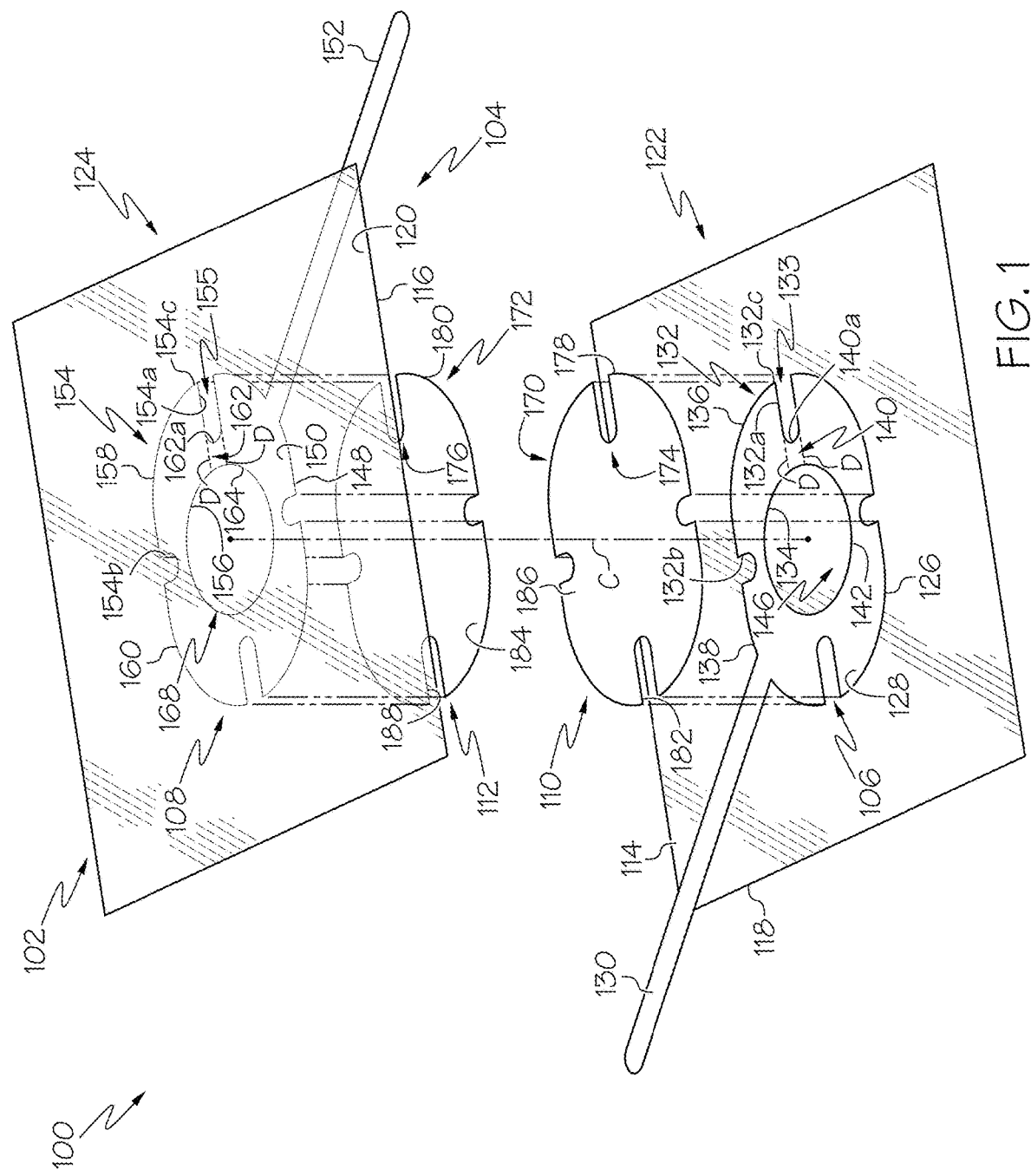
FIG. 1 schematically depicts an exploded view of an example artificial muscle, according to one or more embodiments shown and described herein.

Embodiments described herein are directed to artificial muscles and artificial muscle assemblies. The artificial muscles described herein are actuatable to selectively raise and lower a region of the artificial muscles to provide a selective, on demand inflated expandable fluid region. The artificial muscles include a housing and an electrode pair. A dielectric fluid is housed within the housing, and the housing includes an electrode region and an expandable fluid region, where the electrode pair is positioned in the electrode region. The electrode pair includes a first electrode, which may be fixed to a first surface of the housing and a second electrode, which may be fixed to a second surface of the housing. The electrode pair is actuatable between a non-actuated state and an actuated state such that actuation from the non-actuated state to the actuated state directs the dielectric fluid into the expandable fluid region. This expands the expandable fluid region, raising a portion of the artificial muscle on demand. Further, artificial muscles include one or more clamping devices configured to apply a force against the first electrode and the second electrode to reduce a gap or space therebetween. Due to the reduced gap between a distal end of the first electrode and the second electrode opposite the expandable fluid region, a reduced voltage is required to actuate the artificial muscles. Various embodiments of the artificial muscles and the operation of the artificial muscles are described in more detail herein. Whenever possible, the same reference numerals will be used throughout the drawings to refer to the same or like parts.

Figure 2:
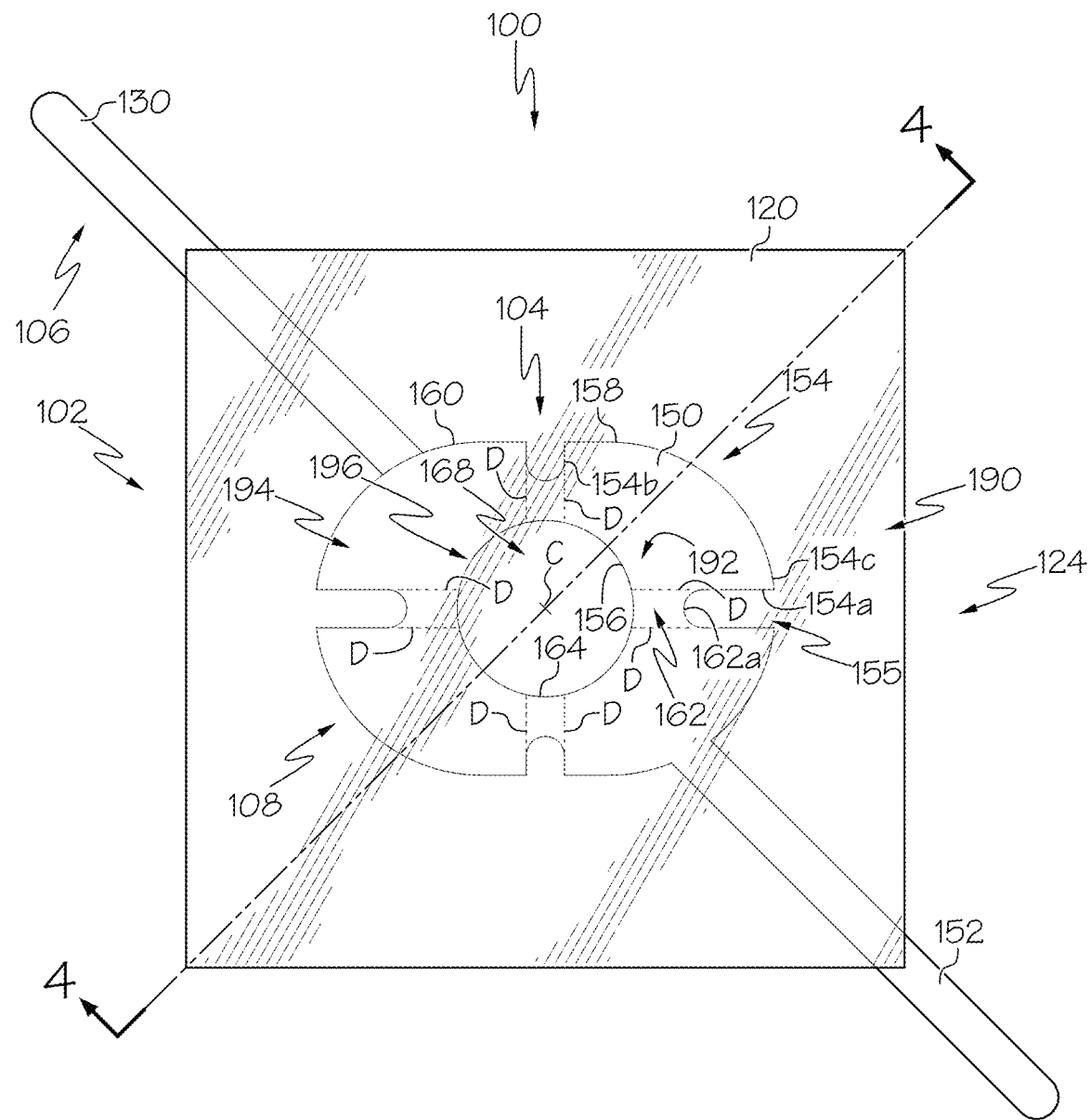
FIG. 2 schematically depicts a top view of the artificial muscle of FIG. 1, according to one or more embodiments shown and described herein.

Referring now to FIGS. 1 and 2, an artificial muscle 100 is shown. The artificial muscle 100 includes a housing 102, an electrode pair 104, including a first electrode 106 and a second electrode 108, fixed to opposite surfaces of the housing 102, a first electrical insulator layer 110 fixed to the first electrode 106, and a second electrical insulator layer 112 fixed to the second electrode 108. In some embodiments, the housing 102 is a one-piece monolithic layer including a pair of opposite inner surfaces, such as a first inner surface 114 and a second inner surface 116, and a pair of opposite outer surfaces, such as a first outer surface 118 and a second outer surface 120. In some embodiments, the first inner surface 114 and the second inner surface 116 of the housing 102 are heat-sealable. In other embodiments, the housing 102 may be a pair of individually fabricated film layers, such as a first film layer 122 and a second film layer 124. Thus, the first film layer 122 includes the first inner surface 114 and the first outer surface 118, and the second film layer 124 includes the second inner surface 116 and the second outer surface 120.

Throughout the ensuing description, reference may be made to the housing 102 including the first film layer 122 and the second film layer 124, as opposed to the one-piece housing. It should be understood that either arrangement is contemplated. In some embodiments, the first film layer 122 and the second film layer 124 generally include the same structure and composition. For example, in some embodiments, the first film layer 122 and the second film layer 124 each comprises biaxially oriented polypropylene (BOPP).

The first electrode 106 and the second electrode 108 are each positioned between the first film layer 122 and the second film layer 124. In some embodiments, the first electrode 106 and the second electrode 108 are each aluminum-coated polyester such as, for example, Mylar®. In addition, one of the first electrode 106 and the second electrode 108 is a negatively charged electrode and the other of the first electrode 106 and the second electrode 108 is a positively charged electrode. For purposes discussed herein, either electrode 106, 108 may be positively charged so long as the other electrode 106, 108 of the artificial muscle 100 is negatively charged.

Figure 12:
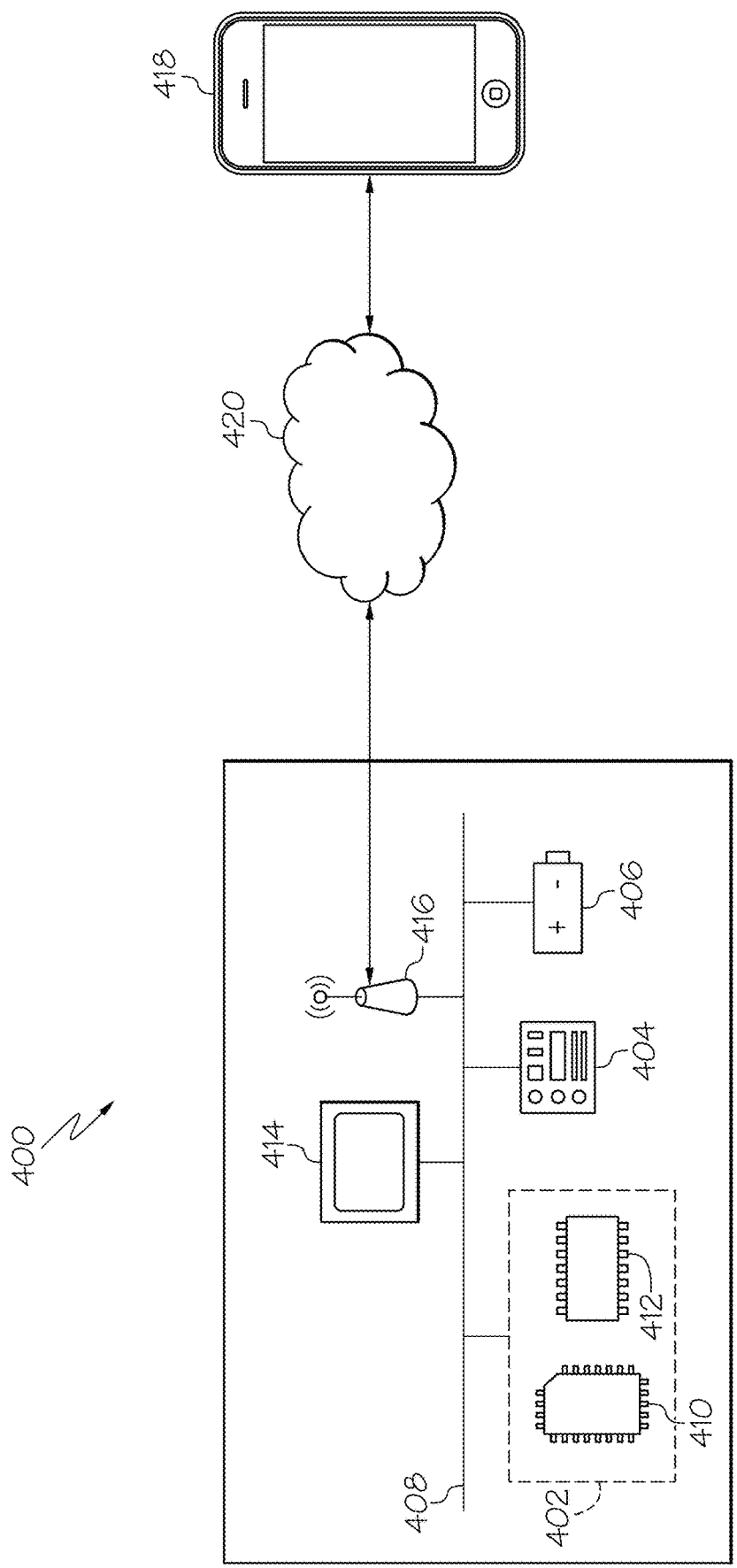
FIG. 12 schematically depicts an actuation system for operating the artificial muscle of FIG. 1, according to one or more embodiments shown and described herein.

The first electrode 106 has a film-facing surface 126 and an opposite inner surface 128. The first electrode 106 is positioned against the first film layer 122, specifically, the first inner surface 114 of the first film layer 122. In addition, the first electrode 106 includes a first terminal 130 extending from the first electrode 106 past an edge of the first film layer 122 such that the first terminal 130 can be connected to a power supply to actuate the first electrode 106. Specifically, the first terminal 130 is coupled, either directly or in series, to a power supply and a controller of an actuation system 400, as shown in FIG. 12. Similarly, the second electrode 108 has a film-facing surface 148 and an opposite inner surface 150. The second electrode 108 is positioned against the second film layer 124, specifically, the second inner surface 116 of the second film layer 124. The second electrode 108 includes a second terminal 152 extending from the second electrode 108 past an edge of the second film layer 124 such that the second terminal 152 can be connected to a power supply and a controller of the actuation system 400 to actuate the second electrode 108.

With respect now to the first electrode 106, the first electrode 106 includes two or more fan portions 132 extending radially from a center axis C of the artificial muscle 100. In some embodiments, the first electrode 106 includes only two fan portions 132 positioned on opposite sides or ends of the first electrode 106. In some embodiments, the first electrode 106 includes more than two fan portions 132, such as three, four, or five fan portions 132. In embodiments in which the first electrode 106 includes an even number of fan portions 132, the fan portions 132 may be arranged in two or more pairs of fan portions 132. As shown in FIG. 1, the first electrode 106 includes four fan portions 132. In this embodiment, the four fan portions 132 are arranged in two pairs of fan portions 132, where the two individual fan portions 132 of each pair are diametrically opposed to one another.

Each fan portion 132 has a first side edge 132a and an opposite second side edge 132b. Each fan portion 132 also has a first end 134 and an opposite second end 136 extending between the first side edge 132a and the second side edge 132b. As shown, the first terminal 130 extends from the second end 136 of one of the fan portions 132 and is integrally formed therewith. A channel 133 is at least partially defined by opposing side edges 132a, 132b of adjacent fan portions 132 and, thus, extends radially toward the center axis C. The channel 133 terminates at an end 140a of a bridge portion 140 interconnecting adjacent fan portions 132.

As shown in FIG. 1, dividing lines D are included to depict the boundary between the fan portions 132 and the bridge portions 140. The dividing lines D extend from the side edges 132a, 132b of the fan portions 132 to the first end 134 of the fan portions 132 collinear with the side edges 132a, 132b. It should be understood that dividing lines D are shown in FIG. 1 for clarity and that the fan portions 132 are integral with the bridge portions 140. The first end 134 of the fan portion 132, which extends between adjacent bridge portions 140, defines an inner length of the fan portion 132. Due to the geometry of the fan portion 132 tapering toward the center axis C between the first side edge 132a and the second side edge 132b, the second end 136 of the fan portion 132 defines an outer length of the fan portion 132 that is greater than the inner length of the fan portion 132.

Moreover, each fan portion 132 has a pair of corners 132c defined by an intersection of the second end 136 and each of the first side edge 132a and the second side edge 132b of the fan portion 132. In embodiments, the corners 132c are formed at an angle equal to or less than 90 degrees. In other embodiments, the corners 132c are formed at an acute angle.

As shown in FIG. 1, each fan portion 132 has a first side length defined by a distance between the first end 134 of the fan portion 132 and the second end 136 of the fan portion 132 along the first side edge 132a and the dividing line D that is collinear with the first side edge 132a. Each fan portion 132 also has a second side length defined by a distance between the first end 134 of the fan portion 132 and the second end 136 of the fan portion 132 along the second side edge 132b and the dividing line D that is collinear with the second side edge 132b. In embodiments, the first side length is greater than the second side length of the fan portion 132 such that the first electrode 106 has an ellipsoid geometry.

The second end 136, the first side edge 132a and the second side edge 132b of each fan portion 132, and the bridge portions 140 interconnecting the fan portions 132 define an outer perimeter 138 of the first electrode 106. In embodiments, a central opening 146 is formed within the first electrode 106 between the fan portions 132 and the bridge portions 140, and is coaxial with the center axis C. Each fan portion 132 has a fan length extending from a perimeter 142 of the central opening 146 to the second end 136 of the fan portion 132. Each bridge portion 140 has a bridge length extending from a perimeter 142 of the central opening 146 to the end 140a of the bridge portion 140, i.e., the channel 133. As shown, the bridge length of each of the bridge portions 140 is substantially equal to one another. Each channel 133 has a channel length defined by a distance between the end 140a of the bridge portion 140 and the second end 136 of the fan portion 132. Due to the bridge length of each of the bridge portions 140 being substantially equal to one another and the first side length of the fan portions 132 being greater than the second side length of the fan portions 132, a first pair of opposite channels 133 has a channel length greater than a channel length of a second pair of opposite channels 133. As shown, a width of the channel 133 extending between opposing side edges 132a, 132b of adjacent fan portions 132 remains substantially constant due to opposing side edges 132a, 132b being substantially parallel to one another.

In embodiments, the central opening 146 has a radius of 2 centimeters (cm) to 5 cm. In embodiments, the central opening 146 has a radius of 3 cm to 4 cm. In embodiments, a total fan area of each of the fan portions 132 is equal to or greater than twice an area of the central opening 146. It should be appreciated that the ratio between the total fan area of the fan portions 132 and the area of the central opening 146 is directly related to a total amount of deflection of the first film layer 122 when the artificial muscle 100 is actuated, as discussed herein. In embodiments, the bridge length is 20% to 50% of the fan length. In embodiments, the bridge length is 30% to 40% of the fan length. In embodiments in which the first electrode 106 does not include the central opening 146, the fan length and the bridge length may be measured from a perimeter of an imaginary circle coaxial with the center axis C.

Similar to the first electrode 106, the second electrode 108 includes two or more fan portions 154 extending radially from the center axis C of the artificial muscle 100. The second electrode 108 includes substantially the same structure as the first electrode 106 and, thus, includes the same number of fan portions 154. Specifically, the second electrode 108 is illustrated as including four fan portions 154. However, it should be appreciated that the second electrode 108 may include any suitable number of fan portions 154.

Each fan portion 154 of the second electrode 108 has a first side edge 154a and an opposite second side edge 154b. Each fan portion 154 also has a first end 156 and an opposite second end 158 extending between the first side edge 154a and the second side edge 154b. As shown, the second terminal 152 extends from the second end 158 of one of the fan portions 154 and is integrally formed therewith. A channel 155 is at least partially defined by opposing side edges 154a, 154b of adjacent fan portions 154 and, thus, extends radially toward the center axis C. The channel 155 terminates at an end 162a of a bridge portion 162 interconnecting adjacent fan portions 154.

As shown in FIG. 1, additional dividing lines D are included to depict the boundary between the fan portions 154 and the bridge portions 162. The dividing lines D extend from the side edges 154a, 154b of the fan portions 154 to the first end 156 of the fan portions 154 collinear with the side edges 154a, 154b. It should be understood that dividing lines D are shown in FIG. 1 for clarity and that the fan portions 154 are integral with the bridge portions 162. The first end 156 of the fan portion 154, which extends between adjacent bridge portions 162, defines an inner length of the fan portion 154. Due to the geometry of the fan portion 154 tapering toward the center axis C between the first side edge 154a and the second side edge 154b, the second end 158 of the fan portion 154 defines an outer length of the fan portion 154 that is greater than the inner length of the fan portion 154.

Moreover, each fan portion 154 has a pair of corners 154c defined by an intersection of the second end 158 and each of the first side edge 154a and the second side edge 154b of the fan portion 154. In embodiments, the corners 154c are formed at an angle equal to or less than 90 degrees. In other embodiments, the corners 154c are formed at an acute angle. As described in more detail herein, during actuation of the artificial muscle 100, the corners 132c of the first electrode 106 and the corners 154c of the second electrode 108 are configured to be attracted to one another at a lower voltage as compared to the rest of the first electrode 106 and the second electrode 108. Thus, actuation of the artificial muscle 100 initially at the corners 132c, 154c results in the outer perimeter 138 of the first electrode 106 and the outer perimeter 160 of the second electrode 108 being attracted to one another at a lower voltage and reducing the likelihood of air pockets or voids forming between the first electrode 106 and the second electrode 108 after actuation of the artificial muscle 100.

As shown in FIGS. 1 and 2, in embodiments, the first side edge 154a of each fan portion 154 has a first side length defined by a distance between the first end 156 of the fan portion 154 and the second end 158 of the fan portion 154 along the first side edge 154a and the dividing line D that is collinear with the first side edge 154a. Each fan portion 154 also has a second side length defined by a distance between the first end 156 of the fan portion 154 and the second end 158 of the fan portion 154 along the second side edge 154b and the dividing line D that is collinear with the second side edge 154b. In embodiments, the first side length is greater than the second side length of the fan portion 154 such that the second electrode 108 has an ellipsoid geometry corresponding to the geometry of the first electrode 106.

The second end 158, the first side edge 154a and the second side edge 154b of each fan portion 154, and the bridge portions 162 interconnecting the fan portions 154 define an outer perimeter 160 of the second electrode 108. In embodiments, a central opening 168 is formed within the second electrode 108 between the fan portions 154 and the bridge portions 162, and is coaxial with the center axis C. Each fan portion 154 has a fan length extending from a perimeter 164 of the central opening 168 to the second end 158 of the fan portion 154. Each bridge portion 162 has a bridge length extending from the central opening 168 to the end 162a of the bridge portion 162, i.e., the channel 155. As shown, the bridge length of each of the bridge portions 162 is substantially equal to one another. Each channel 155 has a channel length defined by a distance between the end 162a of the bridge portion 162 and the second end 158 of the fan portion 154. Due to the bridge length of each of the bridge portions 162 being substantially equal to one another and the first side length of the fan portions 154 being greater than the second side length of the fan portions 154, a first pair of opposite channels 155 has a channel length greater than a channel length of a second pair of opposite channels 155. As shown, a width of the channel 155 extending between opposing side edges 154a, 154b of adjacent fan portions 154 remains substantially constant due to opposing side edges 154a, 154b being substantially parallel to one another.

In embodiments, the central opening 168 has a radius of 2 cm to 5 cm. In embodiments, the central opening 168 has a radius of 3 cm to 4 cm. In embodiments, a total fan area of each of the fan portions 154 is equal to or greater than twice an area of the central opening 168. It should be appreciated that the ratio between the total fan area of the fan portions 154 and the area of the central opening 168 is directly related to a total amount of deflection of the second film layer 124 when the artificial muscle 100 is actuated. In embodiments, the bridge length is 20% to 50% of the fan length. In embodiments, the bridge length is 30% to 40% of the fan length. In embodiments in which the second electrode 108 does not include the central opening 168, the fan length and the bridge length may be measured from a perimeter of an imaginary circle coaxial with the center axis C.

As described herein, the first electrode 106 and the second electrode 108 each have a central opening 146, 168 coaxial with the center axis C. However, it should be understood that the first electrode 106 does not need to include the central opening 146 when the central opening 168 is provided within the second electrode 108, as shown in the embodiment illustrated in FIGS. 6 and 7. Alternatively, the second electrode 108 does not need to include the central opening 168 when the central opening 146 is provided within the first electrode 106.

Referring again to FIG. 1, the first electrical insulator layer 110 and the second electrical insulator layer 112 have a substantially ellipsoid geometry generally corresponding to the geometry of the first electrode 106 and the second electrode 108, respectively. Thus, the first electrical insulator layer 110 and the second electrical insulator layer 112 each have fan portions 170, 172 and bridge portions 174, 176 corresponding to like portions on the first electrode 106 and the second electrode 108. Further, the first electrical insulator layer 110 and the second electrical insulator layer 112 each have an outer perimeter 178, 180 corresponding to the outer perimeter 138 of the first electrode 106 and the outer perimeter 160 of the second electrode 108, respectively, when positioned thereon.

It should be appreciated that, in some embodiments, the first electrical insulator layer 110 and the second electrical insulator layer 112 generally include the same structure and composition. As such, in some embodiments, the first electrical insulator layer 110 and the second electrical insulator layer 112 each include an adhesive surface 182, 184 and an opposite non-sealable surface 186, 188, respectively. Thus, in some embodiments, the first electrical insulator layer 110 and the second electrical insulator layer 112 are each a polymer tape adhered to the inner surface 128 of the first electrode 106 and the inner surface 150 of the second electrode 108, respectively.

Figure 4:
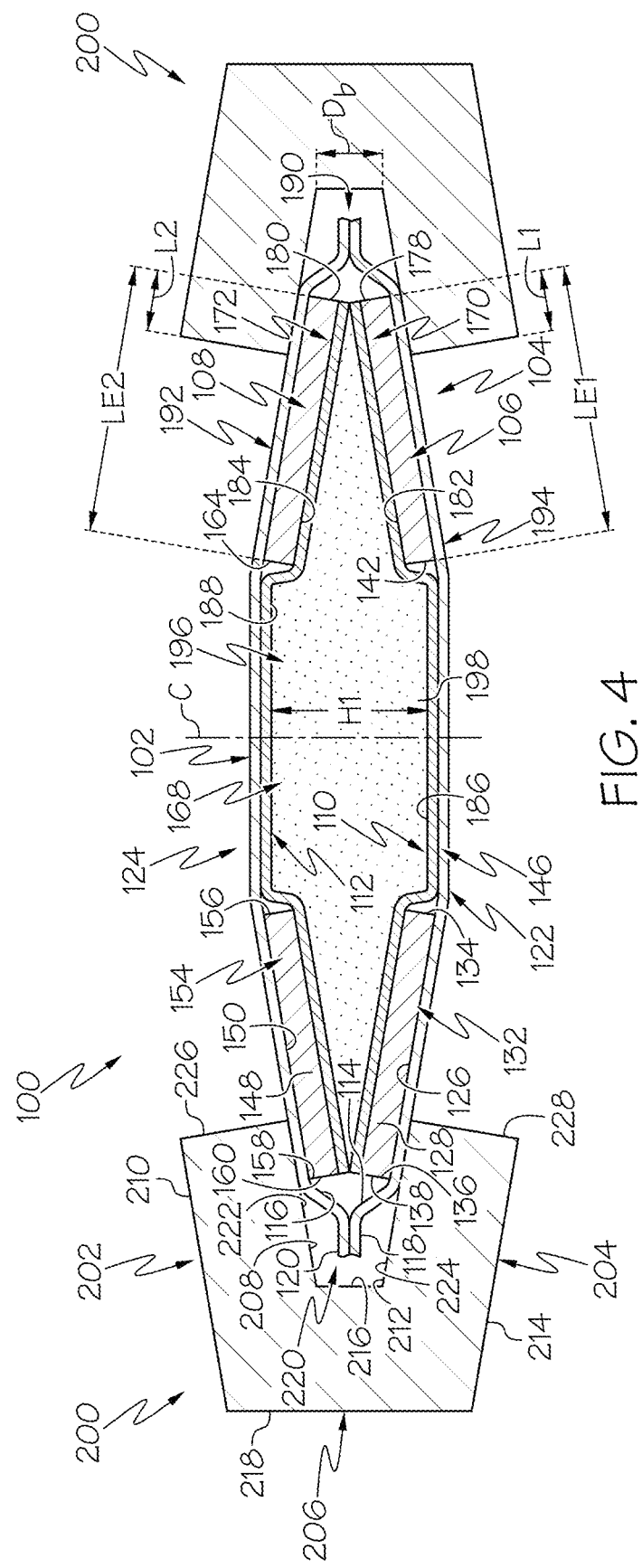
FIG. 4 schematically depicts a cross-sectional view of the artificial muscle of FIG. 1 taken along line 4-4 in FIG. 2 in a non-actuated state and including a plurality of clamping devices, according to one or more embodiments shown and described herein.
Figure 5:
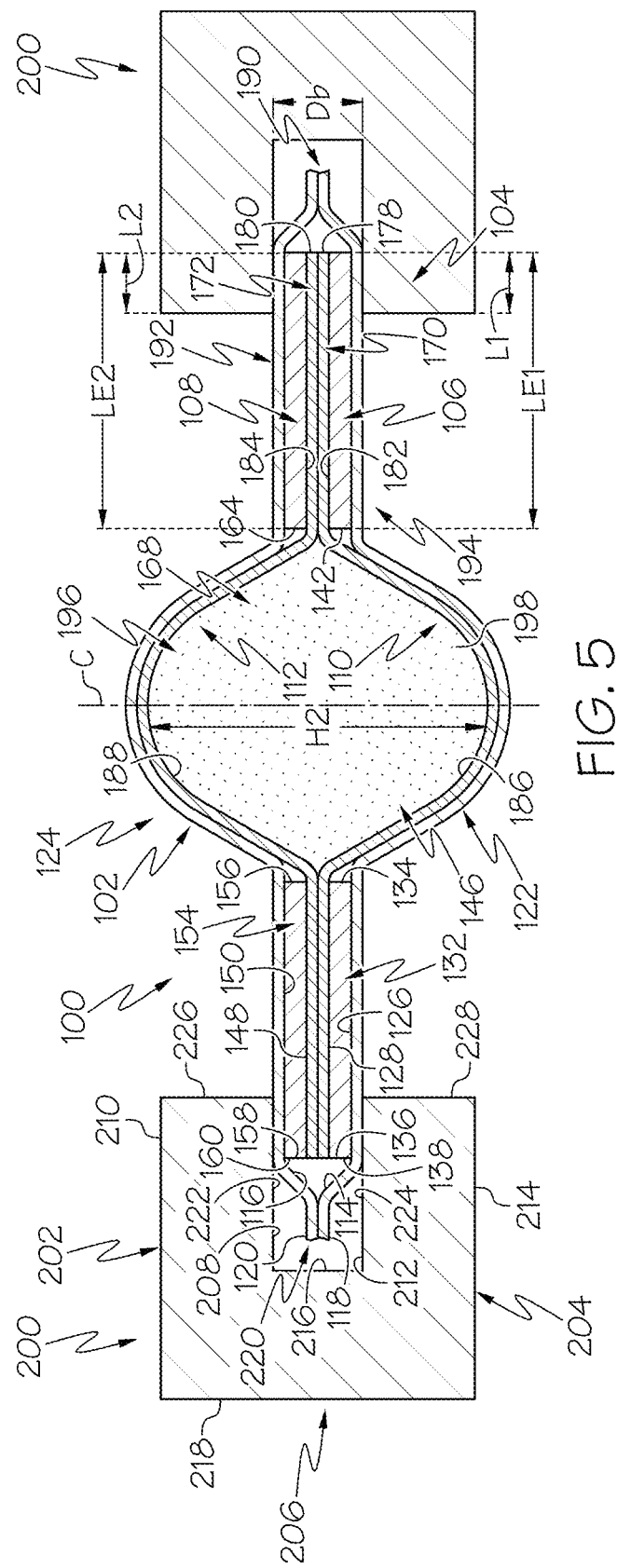
FIG. 5 schematically depicts a cross-sectional view of the artificial muscle of FIG. 4 in an actuated state, according to one or more embodiments shown and described herein.

Referring now to FIGS. 2, 4, and 5, the artificial muscle 100 is shown in its assembled form. As shown in FIG. 2, the second electrode 108 is stacked on top of the first electrode 106 and, therefore, the first electrode 106, the first film layer 122, and the second film layer 124 are not shown. In its assembled form, the first electrode 106, the second electrode 108, the first electrical insulator layer 110, and the second electrical insulator layer 112 are sandwiched between the first film layer 122 and the second film layer 124. The first film layer 122 is partially sealed to the second film layer 124 at an area surrounding the outer perimeter 138 of the first electrode 106 and the outer perimeter 160 of the second electrode 108. In some embodiments, the first film layer 122 is heat-sealed to the second film layer 124. Specifically, in some embodiments, the first film layer 122 is sealed to the second film layer 124 to define a sealed portion 190 surrounding the first electrode 106 and the second electrode 108. The first film layer 122 and the second film layer 124 may be sealed in any suitable manner, such as using an adhesive, heat sealing, vacuum sealing, or the like.

The first electrode 106, the second electrode 108, the first electrical insulator layer 110, and the second electrical insulator layer 112 provide a barrier that prevents the first film layer 122 from sealing to the second film layer 124, thereby forming an unsealed portion 192. The unsealed portion 192 of the housing 102 includes an electrode region 194, in which the electrode pair 104 is provided, and an expandable fluid region 196, which is surrounded by the electrode region 194. The central openings 146, 168 of the first electrode 106 and the second electrode 108 define the expandable fluid region 196 and are arranged to be axially stacked on one another. Although not shown, the housing 102 may be cut to conform to the geometry of the electrode pair 104 and reduce the size of the artificial muscle 100, namely, the size of the sealed portion 190.

A dielectric fluid 198 is provided within the unsealed portion 192 and flows freely between the first electrode 106 and the second electrode 108. A "dielectric" fluid as used herein is a medium or material that transmits electrical force without conduction and as such has low electrical conductivity. Some non-limiting example dielectric fluids include perfluoroalkanes, transformer oils, and deionized water. It should be appreciated that the dielectric fluid 198 may be injected into the unsealed portion 192 of the artificial muscle 100 using a needle or other suitable injection device.

Figure 3:
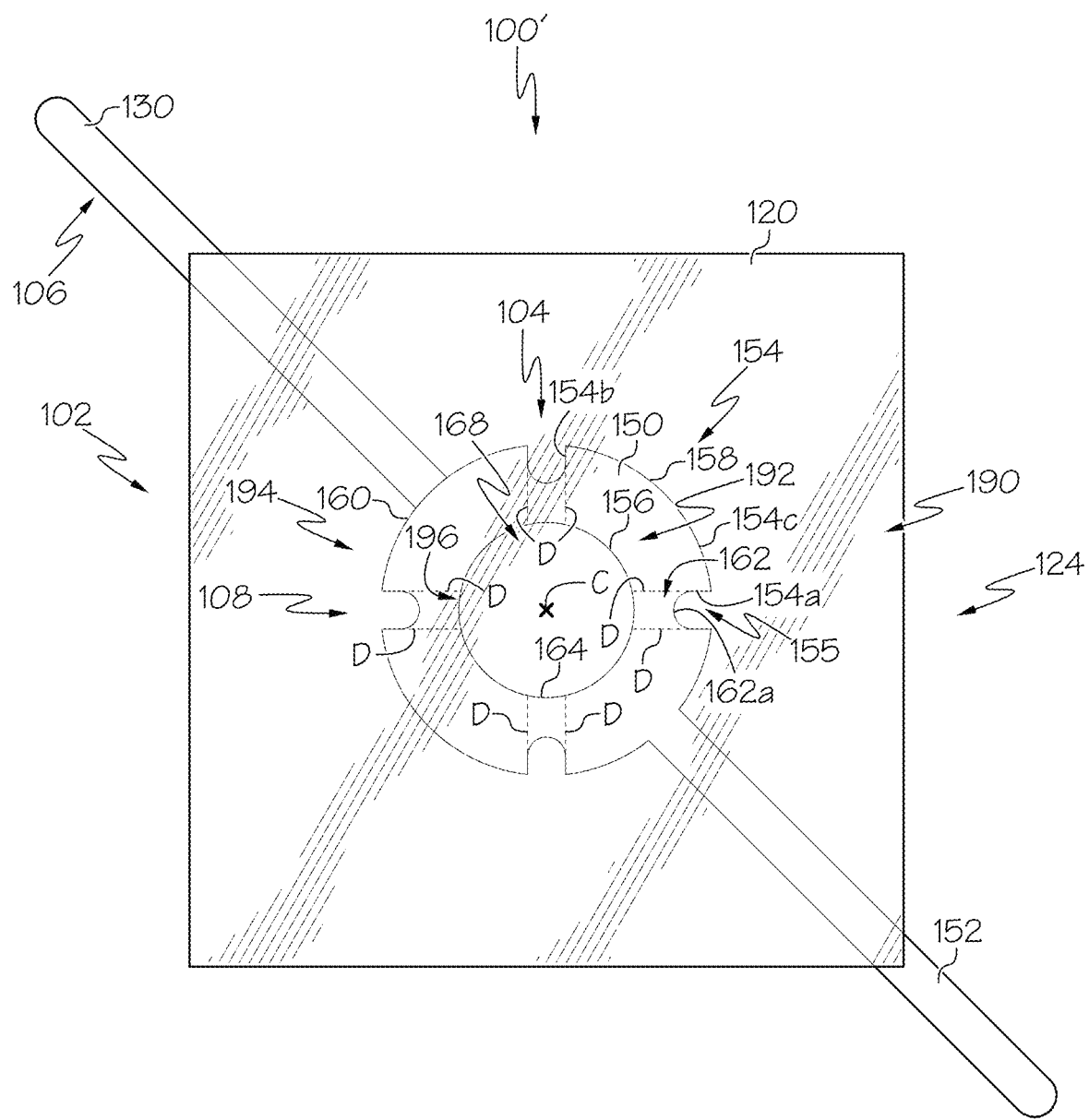
FIG. 3 schematically depicts a top view of another example artificial muscle, according to one or more embodiments shown and described herein.

Referring now to FIG. 3, an alternative embodiment of an artificial muscle 100' is illustrated. It should be appreciated that the artificial muscle 100' is similar to the artificial muscle 100 described herein. As such, like structure is indicated with like reference numerals. The first electrode 106 and the second electrode 108 of the artificial muscle 100' have a circular geometry as opposed to the ellipsoid geometry of the first electrode 106 and the second electrode 108 of the artificial muscle 100 described herein. As shown in FIG. 3, with respect to the second electrode 108, a first side edge length of the first side edge 154a is equal to a second side edge length of the second side edge 154b. Accordingly, the channels 155 formed between opposing side edges 154a, 154b of the fan portions 154 each have an equal length. Although the first electrode 106 is hidden from view in FIG. 3 by the second electrode 108, it should be appreciated that the first electrode 106 also has a circular geometry corresponding to the geometry of the second electrode 108.

Referring now to FIGS. 4 and 5, the artificial muscle 100 is actuatable between a non-actuated state and an actuated state. In the non-actuated state, as shown in FIG. 4, the first electrode 106 and the second electrode 108 are partially spaced apart from one another proximate the central openings 146, 168 thereof and the first end 134, 156 of the fan portions 132, 154. The second end 136, 158 of the fan portions 132, 154 remain in position relative to one another due to the housing 102 being sealed at the outer perimeter 138 of the first electrode 106 and the outer perimeter 160 of the second electrode 108. In the actuated state, as shown in FIG. 5, the first electrode 106 and the second electrode 108 are brought into contact with and oriented parallel to one another to force the dielectric fluid 198 into the expandable fluid region 196. This causes the dielectric fluid 198 to flow through the central openings 146, 168 of the first electrode 106 and the second electrode 108 and inflate the expandable fluid region 196.

Referring now to FIG. 4, the artificial muscle 100 is shown in the non-actuated state. The electrode pair 104 is provided within the electrode region 194 of the unsealed portion 192 of the housing 102. The central opening 146 of the first electrode 106 and the central opening 168 of the second electrode 108 are coaxially aligned within the expandable fluid region 196. In the non-actuated state, the first electrode 106 and the second electrode 108 are non-parallel to one another. The first film layer 122 is sealed to the second film layer 124 around the electrode pair 104. Thus, dielectric fluid 198 is provided between the first electrode 106 and the second electrode 108, thereby separating the first end 134, 156 of the fan portions 132, 154 proximate the expandable fluid region 196. Stated another way, a distance between the first end 134 of the fan portion 132 of the first electrode 106 and the first end 156 of the fan portion 154 of the second electrode 108 is greater than a distance between the second end 136 of the fan portion 132 of the first electrode 106 and the second end 158 of the fan portion 154 of the second electrode 108. This results in the electrode pair 104 zippering toward the expandable fluid region 196 when actuated. More particularly, zippering of the electrode pair 104 is initiated at the corners 132c of the first electrode 106 and the corners 154c of the second electrode 108, as discussed herein. In some embodiments, the first electrode 106 and the second electrode 108 may be flexible. Thus, as shown in FIG. 4, the first electrode 106 and the second electrode 108 are convex such that the second ends 136, 158 of the fan portions 132, 154 thereof may remain close to one another, but spaced apart from one another proximate the central openings 146, 168. In the non-actuated state, the expandable fluid region 196 has a first height H1.

In embodiments, the artificial muscle 100 includes one or more clamping devices 200 for compressing outer perimeters 138, 160 of the first electrode 106 and the second electrode 108 toward one another. Specifically, the one or more clamping devices 200 compress the first electrode 106 and the second electrode 108 to reduce the distance between the second end 136 of the fan portion 132 and the second end 158 of the fan portion 154. Particularly, the compression by the clamping device 200 causes the first electrical insulator layer 110 and the second insulator layer 112 to contact one another proximate the outer perimeters 138, 160 of the first electrode 106 and the second electrode 108. It should be appreciated that by compressing the first electrode 106 and the second electrode 108 at the outer perimeters 138, 160, the voltage required to actuate the artificial muscle 100 is reduced as compared to a situation in which a gap or space is provided between the first electrical insulator layer 110 and the second electrical insulator layer 112 at the outer perimeters 138, 160.

As shown in FIG. 4, a pair of clamping devices 200 are shown provided on opposite sides of the artificial muscle 100. However, it should be appreciated that more than two clamping devices 200 may be provided along an outer perimeter of the artificial muscle 100. Each clamping device 200 includes an upper arm 202, an opposite lower arm 204, and a body 206 interconnecting the upper arm 202 and the lower arm 204. The upper arm 202 has an inner surface 208 and an opposite outer surface 210, the lower arm 204 has an inner surface 212 and an opposite outer surface 214, and the body 206 has an inner surface 216 and an opposite outer surface 218. The inner surface 208 of the upper arm 202, the inner surface 212 of the lower arm 204, and the inner surface 216 of the body 206 cooperate to define a cavity 220 configured to receive the housing 102 and a portion of the first electrode 106 and the second electrode 108.

The body 206 of the inner surface 216 of the body 206 of the clamping device 200 has a body distance Db defined between the upper arm 202 and the lower arm 204. In embodiments, the body distance Db is less than 6 mm. In embodiments, the body distance Db is between 1 mm and 6 mm. In embodiments, the body distance Db is between 2 mm and 5 mm. In embodiments, the body distance Db is between 3 mm and 4 mm. The clamping device 200 may be formed from any suitable material such as, for example, metal, plastic, and the like. In embodiments, the inner surface 208 of the upper arm 202 and the inner surface 212 of the lower arm 204 are provided with an adhesive layer 222, 224 to secure the clamping device 200 onto the housing 102.

In embodiments, the clamping device 200 may be formed from a flexible material providing a biasing force. Particularly, as shown in FIG. 4, the body distance Db appears to be less than a distance between a distal end 226 of the upper arm 202 and a distal end 228 of the lower arm 204 opposite the body 206. This is due to the clamping device 200 being formed from a flexible material allowing the upper arm 202 and the lower arm 204 to be expanded away from one another when the artificial muscle 100 is in the non-actuated state, yet provide a biasing force against the first electrode 106 and the second electrode 108. When the artificial muscle 100 is in the actuated state, as shown in FIG. 5, the biasing force of the clamping device 200 allows the upper arm 202 and the lower arm 204 to flex toward one another. However, it should be appreciated that the clamping device 200 may be formed from a ridged material such that the body distance Db remains equal to a distance between the distal end 226 of the upper arm 202 and the distal end 228 of the lower arm 204 opposite the body 206 such that the upper arm 202 and the lower arm 204 are not permitted to flex away from one another, as shown in FIG. 5.

As shown in FIG. 4, the clamping device 200 is positioned relative to the housing 102 such that the lower arm 204 and the upper arm 202 partially extend to overlap the first electrode 106 and the second electrode 108, respectively, in a vertical direction extending parallel to the center axis C. In embodiments, the lower arm 204 extends along the first electrode 106 by a first length L1. In embodiments, the first length L1 is less than 50% of a first electrode length LE1 defined by a distance between the first end 134 and the second end 136 of the first electrode 106. In embodiments, the first length L1 is less than 40% of the first electrode length LE1. In embodiments, the first length L1 is less than 30% of the first electrode length LE1. In embodiments, the first length L1 is between 10% and 30% of the first electrode length LE1. Similarly, the upper arm 202 extends along the second electrode 108 by a second length L2. In embodiments, the first length L1 may be the same as the second length L2. In embodiments, the second length L2 is less than 50% of a second electrode length LE2 defined by a distance between the first end 156 and the second end 158 of the second electrode 108. In embodiments, the second length L2 is less than 40% of the second electrode length LE2. In embodiments, the second length L2 is less than 30% of the second electrode length LE2. In embodiments, the second length L2 is between 10% and 30% of the second electrode length LE2.

When actuated, as shown in FIG. 5, the clamping device 200 provides a force against the first electrode 106 and the second electrode 108 causing the first electrode 106 and the second electrode 108 to zipper toward one another from the second ends 136, 158 of the fan portions 132, 154 thereof, thereby pushing the dielectric fluid 198 into the expandable fluid region 196. As shown, when in the actuated state, the first electrode 106 and the second electrode 108 are parallel to one another. In the actuated state, the dielectric fluid 198 flows into the expandable fluid region 196 to inflate the expandable fluid region 196. As such, the first film layer 122 and the second film layer 124 expand in opposite directions. In the actuated state, the expandable fluid region 196 has a second height H2, which is greater than the first height H1 of the expandable fluid region 196 when in the non-actuated state. Although not shown, it should be noted that the electrode pair 104 may be partially actuated to a position between the non-actuated state and the actuated state. This would allow for partial inflation of the expandable fluid region 196 and adjustments when necessary.

In order to move the first electrode 106 and the second electrode 108 toward one another, a voltage is applied by a power supply. In some embodiments, a voltage of up to 10 kV may be provided from the power supply to induce an electric field through the dielectric fluid 198. The resulting attraction between the first electrode 106 and the second electrode 108 pushes the dielectric fluid 198 into the expandable fluid region 196. Pressure from the dielectric fluid 198 within the expandable fluid region 196 causes the first film layer 122 and the first electrical insulator layer 110 to deform in a first axial direction along the center axis C of the first electrode 106 and causes the second film layer 124 and the second electrical insulator layer 112 to deform in an opposite second axial direction along the center axis C of the second electrode 108. Once the voltage being supplied to the first electrode 106 and the second electrode 108 is discontinued, the first electrode 106 and the second electrode 108 return to their initial, non-parallel position in the non-actuated state.

It should be appreciated that the present embodiments disclosed herein, specifically, the fan portions 132, 154 with the interconnecting bridge portions 140, 162, provide a number of improvements over actuators, such as HASEL actuators, that do not include the fan portions 132, 154. Embodiments of the artificial muscle 100 including fan portions 132, 154 on each of the first electrode 106 and the second electrode 108, respectively, increases the surface area and, thus, displacement at the expandable fluid region 196 without increasing the amount of voltage required as compared to known HASEL actuators including donut-shaped electrodes having a uniform, radially-extending width. In addition, the corners 132c, 154c of the fan portions 132, 154 of the artificial muscle 100 provide zipping fronts that result in focused and directed zipping along the outer perimeters 138, 160 of the first electrode 106 and the second electrode 108 during actuation as compared to HASEL actuators including donut-shaped electrodes. Specifically, one pair of fan portions 132, 154 provides at least twice the amount of actuator power per unit volume as compared to donut-shaped HASEL actuators, while two pairs of fan portions 132, 154 provide at least four times the amount of actuator power per unit volume. The bridge portions 140, 162 interconnecting the fan portions 132, 154 also limit buckling of the fan portions 132, 154 by maintaining the distance between the channels 133, 155 and the central openings 146, 168. Because the bridge portions 140, 162 are integrally formed with the fan portions 132, 154, the bridge portions 140, 162 also prevent tearing and leakage between the fan portions 132, 154 by eliminating attachment locations that provide an increased risk of rupturing.

In operation, when the artificial muscle 100 is actuated, expansion of the expandable fluid region 196 produces a force of 20 Newton-millimeters (N.mm) per cubic centimeter ($cm^3$) of actuator volume or greater, such as 25 N.mm per $cm^3$ or greater, 30 N.mm per $cm^3$ or greater, 35 N.mm per $cm^3$ or greater, 40 N.mm per $cm^3$ or greater, or the like. In one example, when the artificial muscle 100 is actuated by a voltage of 9.5 kilovolts (kV), the artificial muscle 100 provides a resulting force of 20 N.

Moreover, the size of the first electrode 106 and the second electrode 108 is proportional to the amount of displacement of the dielectric fluid 198. Therefore, when greater displacement within the expandable fluid region 196 is desired, the size of the electrode pair 104 is increased relative to the size of the expandable fluid region 196. It should be appreciated that the size of the expandable fluid region 196 is defined by the central openings 146, 168 in the first electrode 106 and the second electrode 108. Thus, the degree of displacement within the expandable fluid region 196 may alternatively, or in addition, be controlled by increasing or reducing the size of the central openings 146, 168.

Figure 6:
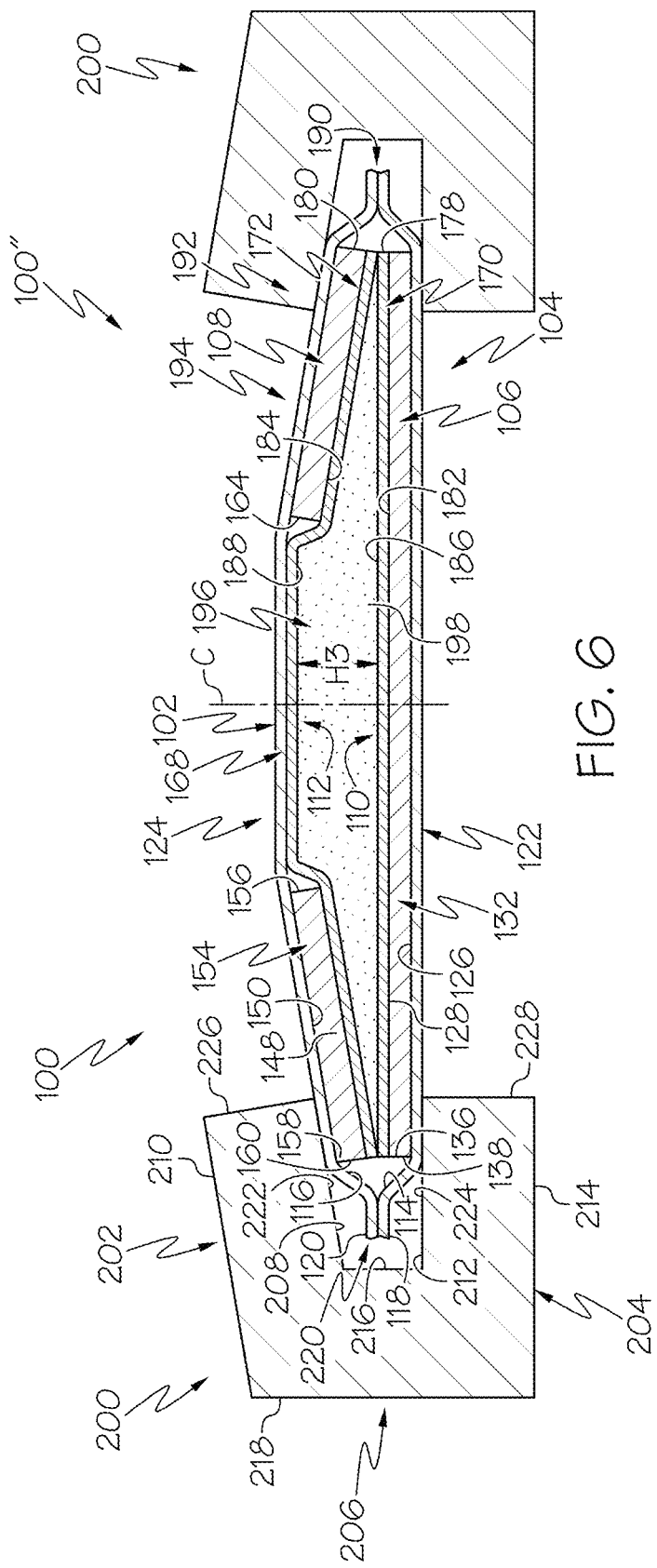
FIG. 6 schematically depicts a cross-sectional view of another example artificial muscle in a non-actuated state, according to one or more embodiments shown and described herein.
Figure 7:
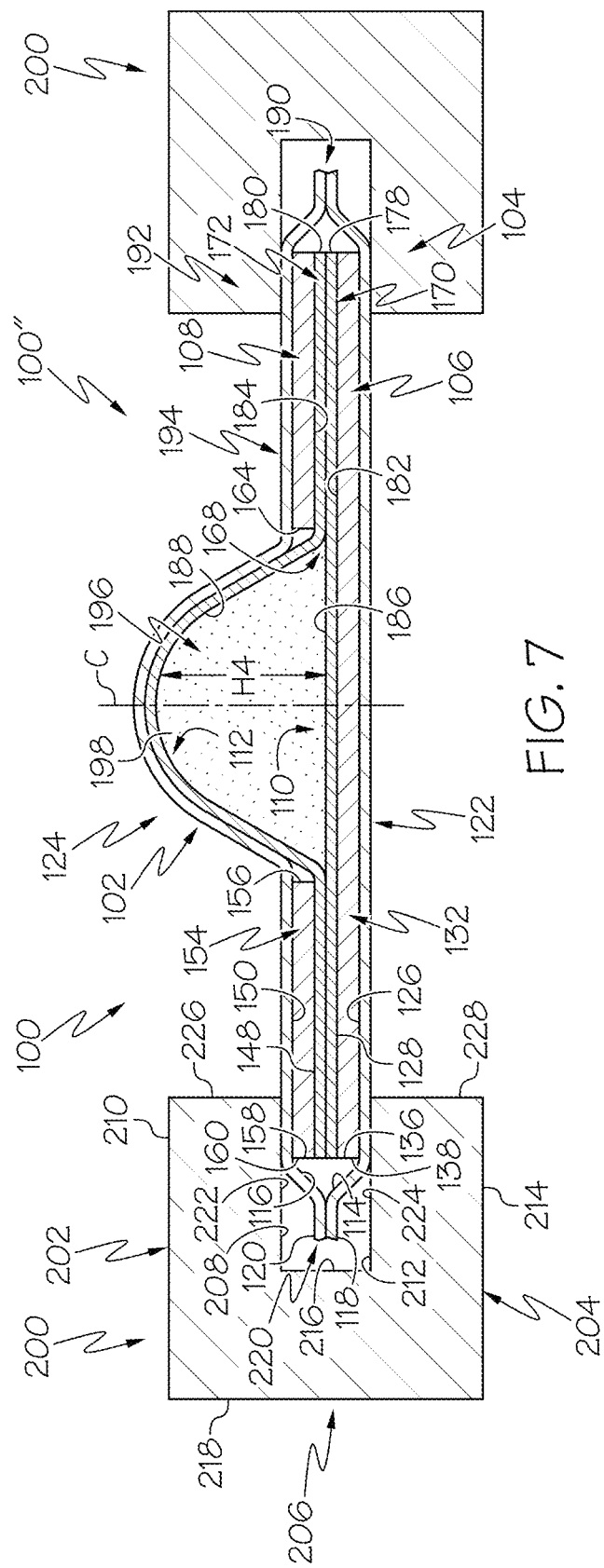
FIG. 7 schematically depicts a cross-sectional view of the artificial muscle of FIG. 6 in an actuated state, according to one or more embodiments shown and described herein.

As shown in FIGS. 6 and 7, another embodiment of an artificial muscle 100" including the pair of clamping devices 200 is illustrated. The artificial muscle 100" is substantially similar to the artificial muscle 100. As such, like structure is indicated with like reference numerals. However, as shown, the first electrode 106 does not include a central opening, such as the central opening 146. Thus, only the second electrode 108 includes the central opening 168 formed therein. As shown in FIG. 6, the artificial muscle 100" is in the non-actuated state with the first electrode 106 being planar and the second electrode 108 being convex relative to the first electrode 106. In the non-actuated state, the expandable fluid region 196 has a first height H3. In the actuated state, as shown in FIG. 7, the expandable fluid region 196 has a second height H4, which is greater than the first height H3. It should be appreciated that by providing the central opening 168 only in the second electrode 108 as opposed to both the first electrode 106 and the second electrode 108, the total deformation may be formed on one side of the artificial muscle 100". In addition, because the total deformation is formed on only one side of the artificial muscle 100", the second height H4 of the expandable fluid region 196 of the artificial muscle 100" extends further from a longitudinal axis perpendicular to the center axis C of the artificial muscle 100" than the second height H2 of the expandable fluid region 196 of the artificial muscle 100 when all other dimensions, orientations, and volume of dielectric fluid are the same.

Figure 8:
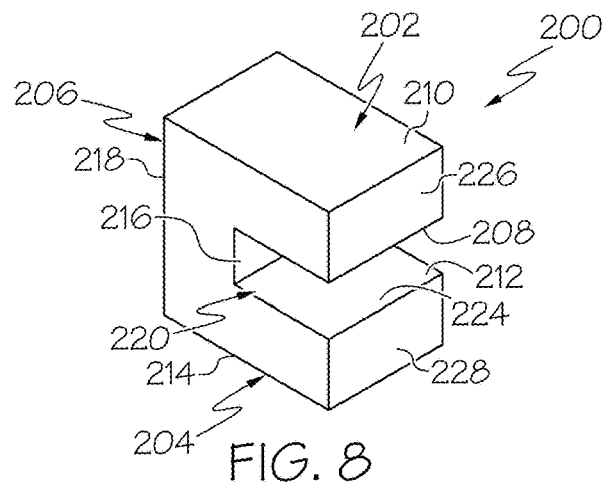
FIG. 8 schematically depicts a perspective view of the clamping device of the artificial muscle of FIG. 4, according to one or more embodiments shown and described herein.
Figure 9:
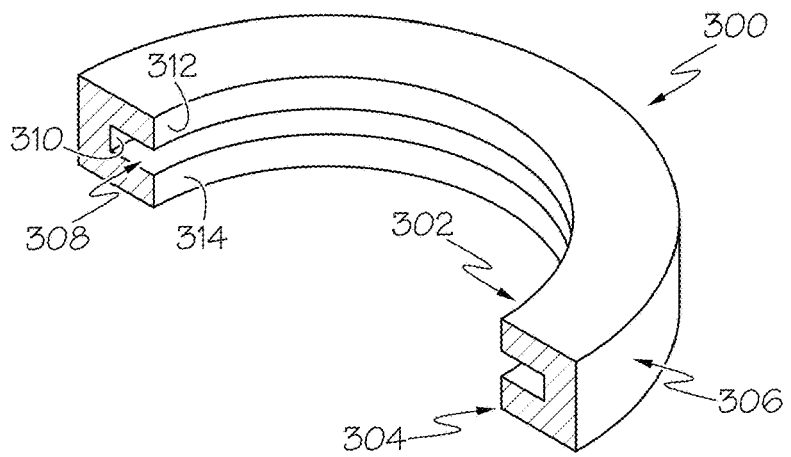
FIG. 9 schematically depicts a partial perspective view of an embodiment of a clamping device, according to one or more embodiments shown and described herein.

Referring to FIG. 8, the clamping device 200 is shown apart from the artificial muscles 100, 100". Referring now to FIG. 9, a partial view of another clamping device 300 is shown. Although only a portion of the clamping device 300 is shown, it should be appreciated that the clamping device 300 is substantially a ring-shaped member to completely encircle an artificial muscle. As such, only a single clamping device 300 is utilized as opposed to a plurality of individual clamping devices 200. Similar to the clamping device 200, the clamping device 300 includes like structure such as, an upper arm 302, an opposite lower arm 304, and a body 306 extending between the upper arm 302 and the lower arm 304. The upper arm 302, the lower arm 304, and the body 306 cooperate to define a cavity 308 to receive the housing 102 of the artificial muscle 100. As the clamping device 300 is a ring-shaped member, an inner surface 310 of the body 306 defines a curvature corresponding to the outer perimeter of an artificial muscle, particularly the first electrode 106 and the second electrode 108. Similarly, in embodiments, the upper arm 302 has a distal end 312 and the lower arm 304 has a distal end 314 also defining a ring shape corresponding to the inner surface 310 of the body 306.

Figure 10:
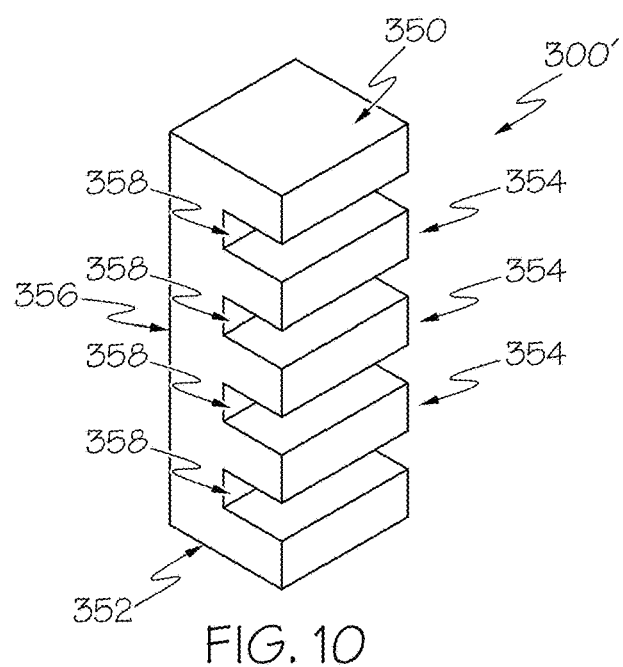
FIG. 10 schematically depicts a perspective view of an embodiment of a clamping device, according to one or more embodiments shown and described herein.
Figure 11:
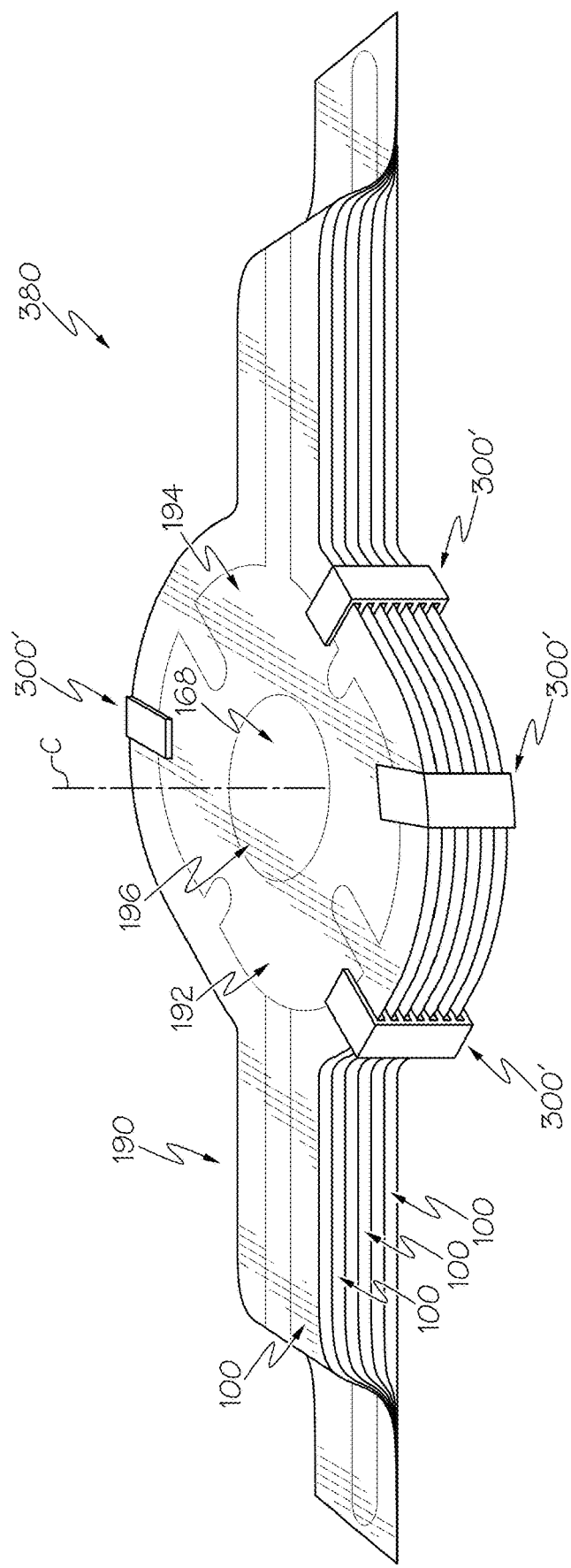
FIG. 11 schematically depicts an artificial muscle assembly including a plurality of the artificial muscles of FIG. 1 and a plurality of the clamping devices of FIG. 10, according to one or more embodiments shown and described herein.

Referring now to FIG. 10, another embodiment of a clamping device 300' is shown. The clamping device 300' includes an upper arm 350, a lower arm 352, at least one intermediate arm 354, and a body 356 interconnecting the upper arm 350, the lower arm 352, and the at least one intermediate arm 354. As shown, the clamping device 300' includes a plurality of intermediate arms 354 arranged between the upper arm 350 and the lower arm 352. As such, the clamping device 300' is similar to the clamping device 200 with the addition of the one or more intermediate arms 354, thereby defining a plurality of cavities 358. It should be appreciated that the clamping device 300' is particularly useful when providing a clamping force on an electrode pair of a plurality of artificial muscles, as illustrated in FIG. 11, such that each cavity 358 is configured to receive a corresponding housing of an artificial muscle stack. It should be appreciated that the features discussed herein with regard to the clamping devices 200, 300, 300' are interchangeable and not specific to any one embodiment.

Referring now to FIG. 11, an artificial muscle assembly 380 is shown including a plurality of artificial muscles, such the artificial muscle 100, and a plurality of clamps 300'. However, it should be appreciated that a plurality of artificial muscles 100' or artificial muscles 100" may similarly be arranged in a stacked formation. Each artificial muscle 100 may be identical in structure and arranged in a stack such that the expandable fluid region 196 of each artificial muscle 100 overlies the expandable fluid region 196 of an adjacent artificial muscle 100. The terminals 130, 152 of each artificial muscle 100 are electrically connected to one another such that the artificial muscles 100 may be simultaneously actuated between the non-actuated state and the actuated state. By arranging the artificial muscles 100 in a stacked configuration, the total deformation of the artificial muscle assembly 380 is the sum of the deformation within the expandable fluid region 196 of each artificial muscle 100. As such, the resulting degree of deformation from the artificial muscle assembly 380 is greater than that which would be provided by the artificial muscle 100 alone.

Referring now to FIG. 12, an actuation system 400 may be provided for operating an artificial muscle or an artificial muscle assembly, such as the artificial muscles 100, 100', 100" or the artificial muscle assembly 380 between the non-actuated state and the actuated state. Thus, the actuation system 400 may include a controller 402, an operating device 404, a power supply 406, and a communication path 408. The various components of the actuation system 400 will now be described.

The controller 402 includes a processor 410 and a non-transitory electronic memory 412 to which various components are communicatively coupled. In some embodiments, the processor 410 and the non-transitory electronic memory 412 and/or the other components are included within a single device. In other embodiments, the processor 410 and the non-transitory electronic memory 412 and/or the other components may be distributed among multiple devices that are communicatively coupled. The controller 402 includes non-transitory electronic memory 412 that stores a set of machine-readable instructions. The processor 410 executes the machine-readable instructions stored in the non-transitory electronic memory 412. The non-transitory electronic memory 412 may comprise RAM, ROM, flash memories, hard drives, or any device capable of storing machine-readable instructions such that the machine-readable instructions can be accessed by the processor 410. Accordingly, the actuation system 400 described herein may be implemented in any conventional computer programming language, as pre-programmed hardware elements, or as a combination of hardware and software components. The non-transitory electronic memory 412 may be implemented as one memory module or a plurality of memory modules.

In some embodiments, the non-transitory electronic memory 412 includes instructions for executing the functions of the actuation system 400. The instructions may include instructions for operating the artificial muscles 100, 100', 100" or the artificial muscle assembly 380 based on a user command.

The processor 410 may be any device capable of executing machine-readable instructions. For example, the processor 410 may be an integrated circuit, a microchip, a computer, or any other computing device. The non-transitory electronic memory 412 and the processor 410 are coupled to the communication path 408 that provides signal interconnectivity between various components and/or modules of the actuation system 400. Accordingly, the communication path 408 may communicatively couple any number of processors with one another, and allow the modules coupled to the communication path 408 to operate in a distributed computing environment. Specifically, each of the modules may operate as a node that may send and/or receive data. As used herein, the term "communicatively coupled" means that coupled components are capable of exchanging data signals with one another such as, for example, electrical signals via conductive medium, electromagnetic signals via air, optical signals via optical waveguides, and the like.

As schematically depicted in FIG. 12, the communication path 408 communicatively couples the processor 410 and the non-transitory electronic memory 412 of the controller 402 with a plurality of other components of the actuation system 400. For example, the actuation system 400 depicted in FIG. 12 includes the processor 410 and the non-transitory electronic memory 412 communicatively coupled with the operating device 404 and the power supply 406.

The operating device 404 allows for a user to control operation of the artificial muscles 100, 100', 100" or the artificial muscle assembly 380. In some embodiments, the operating device 404 may be a switch, toggle, button, or any combination of controls to provide user operation. As a non-limiting example, a user may actuate the artificial muscles 100, 100', 100" or the artificial muscle assembly 380 into the actuated state by activating controls of the operating device 404 to a first position. While in the first position, the artificial muscles 100, 100', 100" or the artificial muscle assembly 380 will remain in the actuated state. The user may switch the artificial muscles 100, 100', 100" or the artificial muscle assembly 380 into the non-actuated state by operating the controls of the operating device 404 out of the first position and into a second position.

The operating device 404 is coupled to the communication path 408 such that the communication path 408 communicatively couples the operating device 404 to other modules of the actuation system 400. The operating device 404 may provide a user interface for receiving user instructions as to a specific operating configuration of the artificial muscles 100, 100', 100" or the artificial muscle assembly 380. In addition, user instructions may include instructions to operate the artificial muscles 100, 100', 100" or the artificial muscle assembly 380 only at certain conditions.

The power supply 406 (e.g., battery) provides power to the artificial muscles 100, 100', 100" or the artificial muscle assembly 380. In some embodiments, the power supply 406 is a rechargeable direct current power source. It is to be understood that the power supply 406 may be a single power supply or battery for providing power to the artificial muscle 100, 100', 100" or the artificial muscle assembly 380. A power adapter (not shown) may be provided and electrically coupled via a wiring harness or the like for providing power to the artificial muscles 100, 100', 100" or the artificial muscle assembly 380 via the power supply 406.

In some embodiments, the actuation system 400 also includes a display device 414. The display device 414 is coupled to the communication path 408 such that the communication path 408 communicatively couples the display device 414 to other modules of the actuation system 400. The display device 414 may output a notification in response to an actuation state of the artificial muscles 100, 100', 100" or the artificial muscle assembly 380 or indication of a change in the actuation state of the artificial muscles 100, 100', 100" or the artificial muscle assembly 380. Moreover, the display device 414 may be a touchscreen that, in addition to providing optical information, detects the presence and location of a tactile input upon a surface of or adjacent to the display device 414. Accordingly, the display device 414 may include the operating device 404 and receive mechanical input directly upon the optical output provided by the display device 414.

In some embodiments, the actuation system 400 includes network interface hardware 416 for communicatively coupling the actuation system 400 to a portable device 418 via a network 420. The portable device 418 may include, without limitation, a smartphone, a tablet, a personal media player, or any other electric device that includes wireless communication functionality. It is to be appreciated that, when provided, the portable device 418 may serve to provide user commands to the controller 402, instead of the operating device 404. As such, a user may be able to control or set a program for controlling the artificial muscles 100, 100', 100" or the artificial muscle assembly 380 without utilizing the controls of the operating device 404. Thus, the artificial muscles 100, 100', 100" or the artificial muscle assembly 380 may be controlled remotely via the portable device 418 wirelessly communicating with the controller 402 via the network 420.

From the above, it is to be appreciated that defined herein are artificial muscles for inflating or deforming a surface of an object by selectively actuating the artificial muscle to raise and lower a region thereof. This provides a low profile inflation member that may operate on demand.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. An artificial muscle comprising:
   a housing comprising an electrode region and an expandable fluid region;
   an electrode pair positioned in the electrode region of the housing, the electrode pair comprising a first electrode positioned adjacent a first surface of the housing and a second electrode positioned adjacent a second surface of the housing, the first electrode and the second electrode each having a first end proximate the expandable fluid region and a second end opposite the expandable fluid region;
   a dielectric fluid housed within the housing; and
   a clamping device applying a force against the first electrode and the second electrode at opposite sides of the second end of the first electrode and the second electrode,
   wherein the electrode pair is actuatable between a non-actuated state and an actuated state such that actuation from the non-actuated state to the actuated state directs the dielectric fluid into the expandable fluid region.

2. The artificial muscle of claim 1, wherein the clamping device comprises:
   an upper arm having an inner surface and an opposite outer surface;

a lower arm having an inner surface and an opposite outer surface; and a body having an inner surface and an opposite outer surface, the body interconnecting the upper arm and the lower arm;

wherein the inner surface of the upper arm, the inner surface of the lower arm, and the inner surface of the body cooperate to define a cavity, the housing partially received within the cavity.

3. He artificial muscle of claim 1, wherein:

the first electrode and the second electrode each comprise two or more fan portions and two or more bridge portions;

each of the two or more bridge portions interconnects adjacent fan portions; and at least one of the first electrode and the second electrode comprises a central opening positioned between the two or more fan portions and encircling the expandable fluid region.

4. The artificial muscle of claim 3, further comprising a plurality of clamping devices, each clamping device of the plurality of clamping devices positioned at a corresponding one of two or more fan portions of the first electrode and the second electrode.

5. The artificial muscle of claim 1, further comprising a first electrical insulator layer fixed to an inner surface of the first electrode opposite the first surface of the housing and a second electrical insulator layer fixed to an inner surface of the second electrode opposite the second surface of the housing, wherein the first electrical insulator layer and the second electrical insulator layer each includes an adhesive surface and an opposite non-sealable surface.

6. The artificial muscle of claim 5, wherein the clamping device compresses the housing such that the first electrical insulator layer and the second electrical insulator layer contact proximate the second end of the first electrode and the second electrode.

7. The artificial muscle of claim 2, wherein:

the lower arm extends along the first electrode by a first length, the first length is less than 50% of a first electrode length defined by a distance between the first end of the first electrode and the second end of the first electrode; and the upper arm extends along the second electrode by a second length, the second length is less than 50% of a second electrode length defined by a distance between the first end of the second electrode and the second end of the second electrode.

8. The artificial muscle of claim 2, wherein the clamping device is a ring-shaped member.

9. The artificial muscle of claim 2, wherein the clamping device comprises an intermediate arm extending from the body, the clamping device defining a first cavity between the upper arm and the intermediate arm, and a second cavity between the lower arm and the intermediate arm.

10. The artificial muscle of claim 2, wherein the inner surface of the body of the clamping device has a body distance defined between the upper arm and the lower arm, the body distance is less than 6 mm.

11. The artificial muscle of claim 10, wherein the body distance is between 3 mm and 4 mm.

12. An artificial muscle comprising:

a housing comprising an electrode region and an expandable fluid region;

an electrode pair positioned in the electrode region of the housing, the electrode pair comprising a first electrode fixed to a first surface of the housing and a second electrode fixed to a second surface of the housing, at least one of the first electrode and the second electrode comprising a central opening encircling the expandable fluid region, the first electrode and the second electrode each having a first end proximate the expandable fluid region and a second end opposite the expandable fluid region;

a dielectric fluid housed within the housing; and a clamping device applying a force against the first electrode and the second electrode at opposite sides of the second end of the first electrode and the second electrode to reduce a gap between the second end of the first electrode and the second end of the second electrode, wherein the electrode pair is actuatable between a non-actuated state and an actuated state such that actuation from the non-actuated state to the actuated state directs the dielectric fluid into the expandable fluid region.

13. The artificial muscle of claim 12, wherein the clamping device comprises:

an upper arm having an inner surface and an opposite outer surface;

a lower arm having an inner surface and an opposite outer surface; and a body having an inner surface and an opposite outer surface, the body interconnecting the upper arm and the lower arm;

wherein the inner surface of the upper arm, the inner surface of the lower arm, and the inner surface of the body cooperate to define a cavity, the housing partially received within the cavity.

14. The artificial muscle of claim 13, wherein the inner surface of the body of the clamping device has a body distance defined between the upper arm and the lower arm, the body distance is less than 6 mm.

15. The artificial muscle of claim 13, wherein:

the lower arm extends along the first electrode by a first length L1, the first length L1 is less than 50% of a first electrode length defined by a distance between the first end of the first electrode and the second end of the first electrode; and the upper arm extends along the second electrode by a second length, the second length is less than 50% of a second electrode length defined by a distance between the first end of the second electrode and the second end of the second electrode.

16. The artificial muscle of claim 13, wherein the clamping device is a ring-shaped member.

17. The artificial muscle of claim 13, wherein the clamping device comprises an intermediate arm extending from the body, the clamping device defining a first cavity between the upper arm and the intermediate arm, and a second cavity between the lower arm and the intermediate arm.

18. A method for actuating an artificial muscle assembly, the method comprising:

generating a voltage using a power supply electrically coupled to an electrode pair of an artificial muscle, the artificial muscle comprising:

a housing with an electrode region and an expandable fluid region, the electrode pair is positioned in the electrode region of the housing, the electrode pair comprising a first electrode positioned adjacent a first surface of the housing and a second electrode positioned adjacent a second surface of the housing, the first electrode and the second electrode each having a first end proximate the expandable fluid region and a second end opposite the expandable fluid region;
a clamping device applying a force against the first electrode and the second electrode at opposite sides of the second end of the first electrode and the second electrode; and
a dielectric fluid housed within the housing, and applying the voltage to the electrode pair of the artificial muscle, thereby actuating the electrode pair from a non-actuated state and an actuated state such that the dielectric fluid is directed into the expandable fluid region of the housing and expands the expandable fluid region.

19. The method of claim 18, wherein the clamping device comprises:
an upper arm having an inner surface and an opposite outer surface;
a lower arm having an inner surface and an opposite outer surface; and
a body having an inner surface and an opposite outer surface, the body interconnecting the upper arm and the lower arm;
wherein the inner surface of the upper arm, the inner surface of the lower arm, and the inner surface of the body cooperate to define a cavity, the housing partially received within the cavity.

20. The method of claim 19, wherein:
the lower arm extends along the first electrode by a first length, the first length is less than 50% of a first electrode length defined by a distance between the first end of the first electrode and the second end of the first electrode; and
the upper arm extends along the second electrode by a second length, the second length is less than 50% of a second electrode length defined by a distance between the first end of the second electrode and the second end of the second electrode.

* * * * *

UNITED STATES PATENT AND TRADEMARK OFFICE
CERTIFICATE OF CORRECTION

PATENT NO. : 11,731,269 B1
APPLICATION NO. : 17/590376
DATED : August 22, 2023
INVENTOR(S) : Michael P. Rowe It is certified that error appears in the above-identified patent and that said Letters Patent is hereby corrected as shown below:

In the Specification

In Column 9, Line(s) 4, delete "example dielectric" and insert --examples of dielectric--, therefor.

In the Claims

In Column 17, Line(s) 10, Claim 3, delete "He", and insert --The--, therefor.

Signed and Sealed this
Third Day of October, 2023

Katherine Kelly Vidal
*Director of the United States Patent and Trademark Office*